United States Patent
Hong et al.

(10) Patent No.: US 12,351,544 B2
(45) Date of Patent: Jul. 8, 2025

(54) BOROHYDRIDE REDUCTION STABILIZING SYSTEM AND METHOD FOR REDUCING ESTER TO ALCOHOL

(71) Applicant: ASYMCHEM LABORATORIES (TIANJIN) CO., LTD., TEDA Tianjin (CN)

(72) Inventors: Hao Hong, Morrisville, NC (US); Jiangping Lu, Tianjin (CN); Enxuan Zhang, Tianjin (CN); Zhiqing Liu, Tianjin (CN); Tao Zhang, Tianjin (CN)

(73) Assignee: ASYMCHEM LABORATORIES (TIANJIN) CO., LTD., Tianjin (CN)

(*) Notice: Subject to any disclaimer, the term of this patent is extended or adjusted under 35 U.S.C. 154(b) by 782 days.

(21) Appl. No.: 17/618,577

(22) PCT Filed: Jun. 11, 2019

(86) PCT No.: PCT/CN2019/090738
§ 371 (c)(1),
(2) Date: Dec. 13, 2021

(87) PCT Pub. No.: WO2020/248127
PCT Pub. Date: Dec. 17, 2020

(65) Prior Publication Data
US 2022/0259122 A1    Aug. 18, 2022

(51) Int. Cl.
*C07C 29/147*    (2006.01)
*C07B 41/02*    (2006.01)

(52) U.S. Cl.
CPC ............ *C07C 29/147* (2013.01); *C07B 41/02* (2013.01)

(58) Field of Classification Search
CPC ... C07C 29/147; C07C 213/00; C07C 215/28; C07C 205/19; C07C 31/20; C07B 41/02
See application file for complete search history.

(56) References Cited

FOREIGN PATENT DOCUMENTS

| CN | 1554648 A | 12/2004 |
|---|---|---|
| CN | 105237342 A | 1/2016 |
| CN | 107141278 A | 9/2017 |
| CN | 108516922 A | 9/2018 |
| CN | 109153623 A | 1/2019 |
| JP | 2008001631 A | 1/2008 |

OTHER PUBLICATIONS

Prasanth et al., Stabilization of NaBH4 in methanol using a catalytic amount of NaOMe. Reduction of esters and lactones at room temperature without solvent-induced loss of hydride, (The Journal of Organic Chemistry 2018, 83, 1431-1440).*
Antonio Russo, "Unexpected effect of alkoxides on the reactivity of sodium borohydrid in the reduction of perfluoropolyether carboxylic esters", Journal of Fluorine Chemistry 125 (2004) 181-188.
International Search Report for corresponding application PCT/CN2019/090728 filed Jun. 11, 2019; Mail date Mar. 10, 2020.

* cited by examiner

*Primary Examiner* — Jafar F Parsa
(74) *Attorney, Agent, or Firm* — CANTOR COLBURN LLP

(57) ABSTRACT

Disclosed are a borohydride reduction stabilizing system and a method for reducing an ester to an alcohol. The borohydride reduction stabilizing system includes: a borohydride reducing agent and a stabilizing agent for stabilizing the borohydride reducing agent. The borohydride reducing agent is sodium borohydride or potassium borohydride. The stabilizing agent is an alkali metal salt of an alcohol. By adding the alkali metal salt of the alcohol, such as sodium alkoxide or potassium alkoxide, on the basis of an existing sodium/potassium borohydride reducing agent, the sodium/potassium borohydride reducing agent may be kept stable without being decomposed under the condition of increased temperature, so that on the one hand, the reducing activity is maintained in a relatively high state, and the condition of excessive use is reduced, and on the other hand, the generation of hydrogen is reduced, and the process risks are reduced.

12 Claims, No Drawings

BOROHYDRIDE REDUCTION STABILIZING SYSTEM AND METHOD FOR REDUCING ESTER TO ALCOHOL

TECHNICAL FIELD

The present invention relates to the field of ester reduction, and in particular to a borohydride reduction stabilizing system and a method for reducing an ester to an alcohol.

BACKGROUND

In the field of medicines and chemical industries, process synthesis technologies that achieve the reduction of an ester group to an alcohol compound through a continuous reaction technology are often encountered. Reducing the ester group to a corresponding alcohol is an important synthetic method for the conversion of an important functional group in organic synthesis. Commonly used reducing agents are metal hydrides, such as lithium aluminum tetrahydrogen, lithium borohydride, and diisobutyl aluminum hydride. This type of the agents is usually sensitive to water, while sodium borohydride is relatively low sensitive to the water, and has the prospect of industrial application.

However, the sodium borohydride does not have strong reducibility for a part of the ester groups, and it is usually necessary to add Lewis acid to improve the activity of the sodium borohydride, such as LiCl, LiBr, $MgCl_2$, $CaCl_2$, $ZnCl_2$, $ZnBr_2$, $AlCl_3$, $CoCl_2$, $NiCl_2$ and $CeCl_3$ and the like. Or it needs to be performed under heating or reflux conditions, and while the sodium borohydride is in a protic solvent, the sodium borohydride may be decomposed by increasing the temperature.

Therefore, while the sodium borohydride is used as a reducing agent to reduce the ester to the alcohol, there are still the following problems:

(1) The use of the protic solvent causes the decomposition of reducing agents such as the sodium borohydride or the lithium aluminum tetrahydrogen, so the amount of the reducing agent used is increased.

(2) During a quenching process in a batch reaction, the excessive reducing agent may generate a large amount of hydrogen, and the process safety factor is low.

(3) The batch reduction reaction may cause the more hydrogen to be produced in the batch reaction process, and there is a higher process risk in large-scale production, and the batch feeding operation of the reducing agent is cumbersome.

SUMMARY

A main purpose of the present invention is to provide a borohydride reduction stabilizing system and a method for reducing an ester to an alcohol, as to solve a problem in the prior art that sodium/potassium borohydride is easily decomposed while it is used as a reducing agent to reduce the ester to the alcohol.

In order to achieve the above purpose, according to one aspect of the present invention, a borohydride reduction stabilizing system is provided, and the borohydride reduction stabilizing system includes: a borohydride reducing agent, the borohydride reducing agent is sodium borohydride or potassium borohydride; and a stabilizing agent for stabilizing the borohydride reducing agent, the stabilizing agent is an alkali metal salt of an alcohol.

Further, the stabilizing agent is a sodium salt or potassium salt of an alcohol; and preferably, the stabilizing agent is a sodium salt or potassium salt of any one or more alcohols selected from the group consisting of methanol, ethanol, butanol and pentanol; and more preferably, the butanol is tert-butanol, and the pentanol is tert-pentanol.

Further, the molar ratio of the borohydride reducing agent to the stabilizing agent is 1.0-5.0:0.001-0.3, preferably 1.0-2.0:0.01-0.15, and more preferably 1.5-2.0:0.01-0.05.

Further, the borohydride reduction stabilizing system further includes an alcohol solvent; and preferably, the alcohol solvent is a C1-C5 alcohol solvent, more preferably the alcohol solvent is a C1-C3 alcohol solvent, and further preferably methanol solvent, ethanol solvent or isopropyl alcohol solvent.

In order to achieve the above purpose, according to one aspect of the present invention, a method for reducing an ester to an alcohol is provided, the method including reducing an ester to an alcohol with any one of the above borohydride reduction stabilizing systems.

Further, the ester has a structure represented by formula (I):

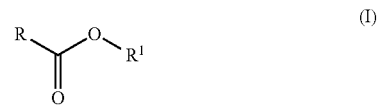

Herein R1 or R is each independently selected from any group or substituted group consisting of: alkyl, heteroalkyl, aryl, heteroaryl, cycloalkyl, heterocycloalkyl, alkyl cycloalkyl, cycloalkyl heteroalkyl, aralkyl and aryl heteroalkyl, and the group has 1~50, preferably 1~20 carbon atoms; or R1 and R form a ring structure.

Further, R1 or R is each independently selected from C1-C18 aralkyl, C1-C18 heteroaralkyl, C1-C18 alkyl, C1-C18 heteroalkyl, or C1-C18 cycloalkyl heteroalkyl, herein a heteroatom in the heteroaralkyl, the heteroalkyl and the cycloalkyl heteroalkyl is N, O and/or S.

Further, R1 is C1-C12 alkyl, R is

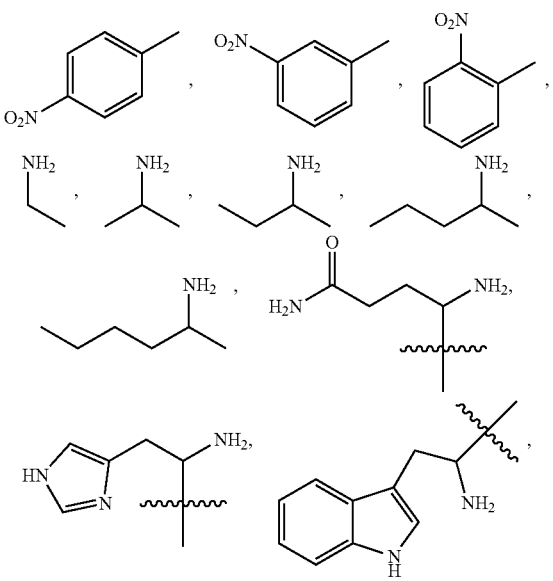

-continued

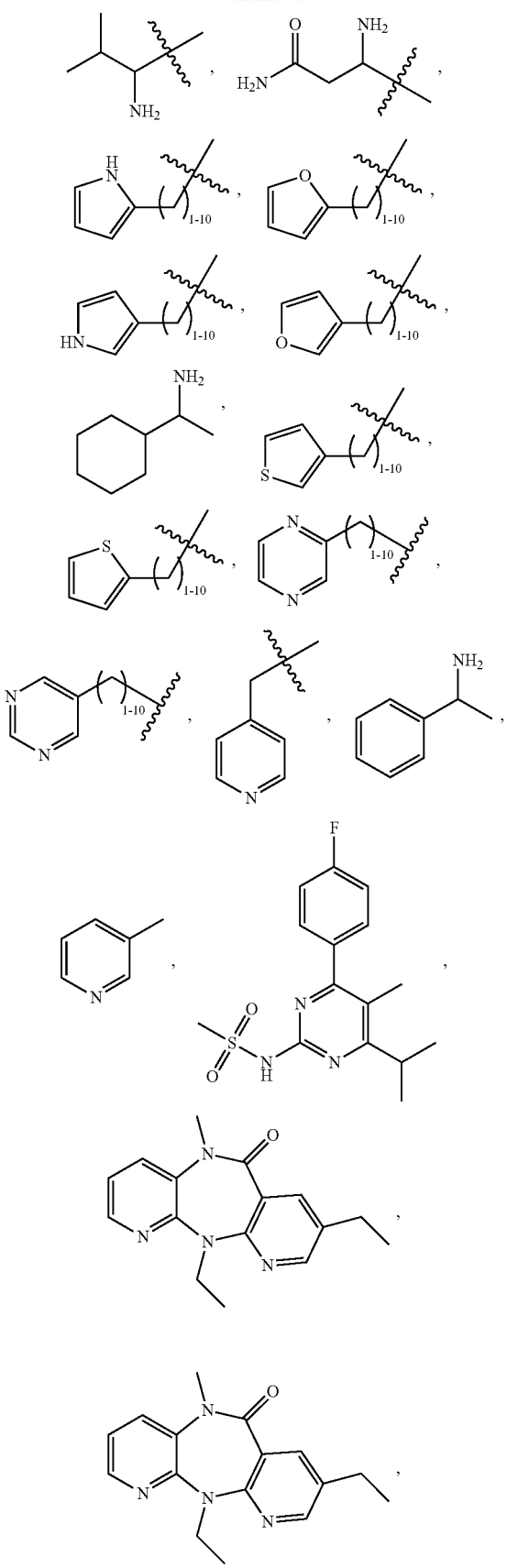

-continued

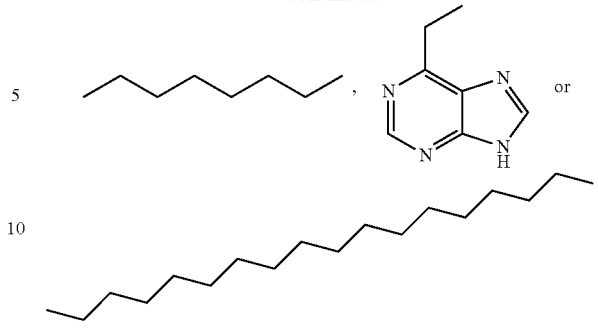

Further, in the borohydride reduction stabilizing system, the molar ratio of the borohydride reducing agent to the ester is 1.0-5.0:1, preferably 1.0-2.0:1, and more preferably 1.5-2.0:1, and preferably, the molar ratio of the stabilizing agent to the ester is 0.001-0.3:1, preferably 0.01-0.15:1, and more preferably 0.01-0.05:1.

Further, the method is a continuous production method; and preferably, the continuous production method includes: continuously adding the ester in parallel with the borohydride reduction stabilizing system to a reactor for reaction, herein the temperature of the reactor is 20~65° C., and preferably 40~60° C., and the retention time of the reaction is 15~120 min, and preferably 20~60 min.

Further, before the step of continuously adding the ester to the reactor, the continuous production method further includes dissolving the ester into an alcohol solvent; and preferably, the alcohol solvent is a C1-C5 alcohol solvent, more preferably, the alcohol solvent is a C1-C3 alcohol solvent, and further preferably, the alcohol solvent is methanol solvent, ethanol solvent or isopropyl alcohol solvent.

A technical scheme of the present invention is applied, by adding the alkali metal salt of the alcohol (such as sodium alkoxide or potassium alkoxide) on the basis of an existing sodium/potassium borohydride reducing agent, the sodium/potassium borohydride reducing agent may be kept stable without being decomposed under the condition of increased temperature, so that on the one hand, the reducing activity is maintained in a relatively high state, and the condition of excessive use is reduced, and on the other hand, the generation of hydrogen is reduced, and the process risks are reduced.

DETAILED DESCRIPTION OF THE EMBODIMENTS

It should be noted that embodiments in the present application and features in the embodiments may be combined with each other in the case without conflicting. The present invention is described in detail below in combination with the embodiments.

Alkyl: refers to a saturated linear or branched hydrocarbon group, a hydrocarbon group of 1~50 carbon atoms, especially a hydrocarbon group of 1~20 carbon atoms, more preferably a hydrocarbon group of 1~12 carbon atoms, and further preferably a hydrocarbon group with 1~8 or 1~6 carbon atoms, specifically it may be methyl, ethyl, propyl, isopropyl, n-butyl, isobutyl, tert-butyl, pentyl, n-hexyl, n-octyl and the like.

Heteroalkyl: refers to an alkyl in which one or more (preferably 1, 2 or 3) carbon atoms are substituted with heteroatoms (including oxygen, nitrogen, phosphorus, silicon or sulfur).

Aryl: refers to a group containing a benzene ring.

Heteroaryl: refers to a group in which a carbon atom on a benzene ring is substituted with a heteroatom.

Cycloalkyl: refers to a cyclic saturated hydrocarbon group with 1~50 carbon atoms, especially 1~20 carbon atoms.

Heterocycloalkyl: refers to a group in which a carbon atom on a cycloalkyl is substituted with a heteroatom.

Alkyl cycloalkyl: refers to a group in which hydrogen on a cycloalkyl is substituted with an alkyl.

Cycloalkyl heteroalkyl: refers to a group in which hydrogen on a heteroalkyl is substituted with a cycloalkyl.

Aralkyl: refers to a group in which hydrogen on an alkyl is substituted with an aryl.

Aryl heteroalkyl: refers to a group in which hydrogen on a heteroalkyl is substituted with an aryl.

The number of carbon atoms of the above various groups is 1~50, especially 1~20.

The above various groups may be substituted groups, it means that one or more hydrogen atoms in the above groups are substituted with other atoms or groups, such as halogen, —OH, —SH, —NH$_2$, —NO$_2$, =O, =S, =NH substituted groups. Specifically, such as trichloroethyl.

As mentioned in the background, the sodium/potassium borohydride in the existing technology is easily decomposed while it is used as a reducing agent for reducing the ester to the alcohol. The inventor improves this type of the reducing agent to make the stability of the sodium/potassium borohydride as the reducing agent in the protic solvent increased, and it may be achieved that various esters may be reduced to corresponding alcohols. In addition, in order to further improve the process safety, the present application uses the reducing agent with the enhanced stability to be applied to the production of continuously reducing the esters to the alcohols, not only the production efficiency is improved, but also the process safety is high.

On the basis of the above research results, the applicant provides the technical scheme of the present application. In a typical implementation mode, a borohydride reduction stabilizing system is provided, and the borohydride reduction stabilizing system includes: a borohydride reducing agent and a stabilizing agent for stabilizing the borohydride reducing agent, the borohydride reducing agent is sodium borohydride or potassium borohydride, and the stabilizing agent is an alkali metal salt of an alcohol.

By adding the alkali metal salt of the alcohol (such as sodium alkoxide or potassium alkoxide) on the basis of an existing sodium/potassium borohydride reducing agent, the sodium/potassium borohydride reducing agent may be kept stable without being decomposed under the condition of increased temperature, so that on the one hand, the reducing activity is maintained in a relatively high state, and the condition of excessive use is reduced, and on the other hand, the generation of hydrogen is reduced, and the process risks are reduced.

The stabilizing agent in the above borohydride reduction stabilizing system is preferably a sodium salt or potassium salt of an alcohol, and the sodium salt or potassium salt of the alcohol is widely used in industry and is inexpensive.

Specifically, the type of the alcohol in the above sodium salt or potassium salt of the alcohol is not particularly limited. In a preferred embodiment of the present application, the stabilizing agent is a sodium salt or potassium salt of any one or more alcohols selected from the group consisting of methanol, ethanol, butanol and pentanol; and more preferably, the butanol is tert-butanol, and the pentanol is tert-pentanol. Alkali metal salts of these types of the alcohols may increase the stability of the borohydride in protic alcohol solvents, thereby it is beneficial to reduce the amount of the borohydride used and increase the conversion rate of the reaction.

In order to stabilize the borohydride reducing agent more effectively, the inventor also, according to the ratio of the amount of the borohydride reducing agent to a substrate, and the ratio of the amount of the stabilizing agent to the substrate, optimizes the ratio of the amount of the borohydride reducing agent to the stabilizing agent. In a preferred embodiment of the present application, the molar ratio of the borohydride reducing agent to the stabilizing agent is 1.0-5.0:0.001-0.3, preferably 1.0-2.0:0.01-0.15, more preferably 1.5-2.0:0.01-0.05. While the molar ratio of the stabilizing agent to the borohydride reducing agent is within the above preferred range, the stabilizing effect is better.

Since the borohydride reduction stabilizing system provided by the present application is improved for the situation that the sodium/potassium borohydride as a reducing agent is easily decomposed in the protic solvent, the borohydride reduction stabilizing system also includes an alcohol solvent. The alcohol solvent here is preferably selected from a C1-C5 alcohol solvent, more preferably the alcohol solvent is a C1-C3 alcohol solvent, and further preferably a methanol solvent, an ethanol solvents or an isopropanol solvent. The alcohol solvent of which the carbon number is within this range is selected to increase the solubility of the borohydride, and achieve a homogeneous reaction, and it is convenient for the continuous reaction.

The amount of the alcohol solvent in the above borohydride reduction stabilizing system is reasonably set according to the amount of an ester substrate to be reduced by the system. In a preferred embodiment, the concentration-volume ratio of the substrate to the alcohol solvent is 1 g:3-10 mL. While the amount ratio of the alcohol solvent to the substrate is within the above range, the raw material conversion rate and yield may be improved.

In another typical implementation mode of the present application, a method for reducing an ester to an alcohol is provided. The method includes reducing the ester to the alcohol with any one of the above borohydride reduction stabilizing systems. The improved borohydride reduction stabilizing system of the present application is used to reduce the ester. The cheap sodium alkoxide may increase the stability of the sodium borohydride in a protic solvent such as methanol, and the post-treatment is simple, the alcohol solvent may be recycled, and the production cost is reduced.

The improved borohydride reduction stabilizing system of the present application stabilizes the reducibility of the sodium/potassium borohydride as a reducing agent in the protic solvent, so that various existing ester substrates may be reduced to corresponding alcohols. In the present application, the specific type of the above ester substrates is not particularly limited, and it may be any ester substances.

In a preferred embodiment, the ester has a structure represented by formula (I):

(I)

Herein R1 or R is each independently H, or any group or substituted group consisting of alkyl, heteroalkyl, aryl, heteroaryl, cycloalkyl, heterocycloalkyl, alkyl cycloalkyl, cycloalkyl heteroalkyl, aralkyl and aryl heteroalkyl, and the group has 1~50, preferably 1~20 carbon atoms; or R1 and R form a ring structure.

In a preferred embodiment, R1 or R is each independently selected from C1-C18 aralkyl, C1-C18 heteroaralkyl, C1-C18 alkyl, C1-C18 heteroalkyl, or C1-C18 cycloalkyl heteroalkyl, herein a heteroatom in the heteroaralkyl, the heteroalkyl and the cycloalkyl heteroalkyl is N, O and/or S.

In a preferred embodiment, R1 is C1-C12 alkyl, R is

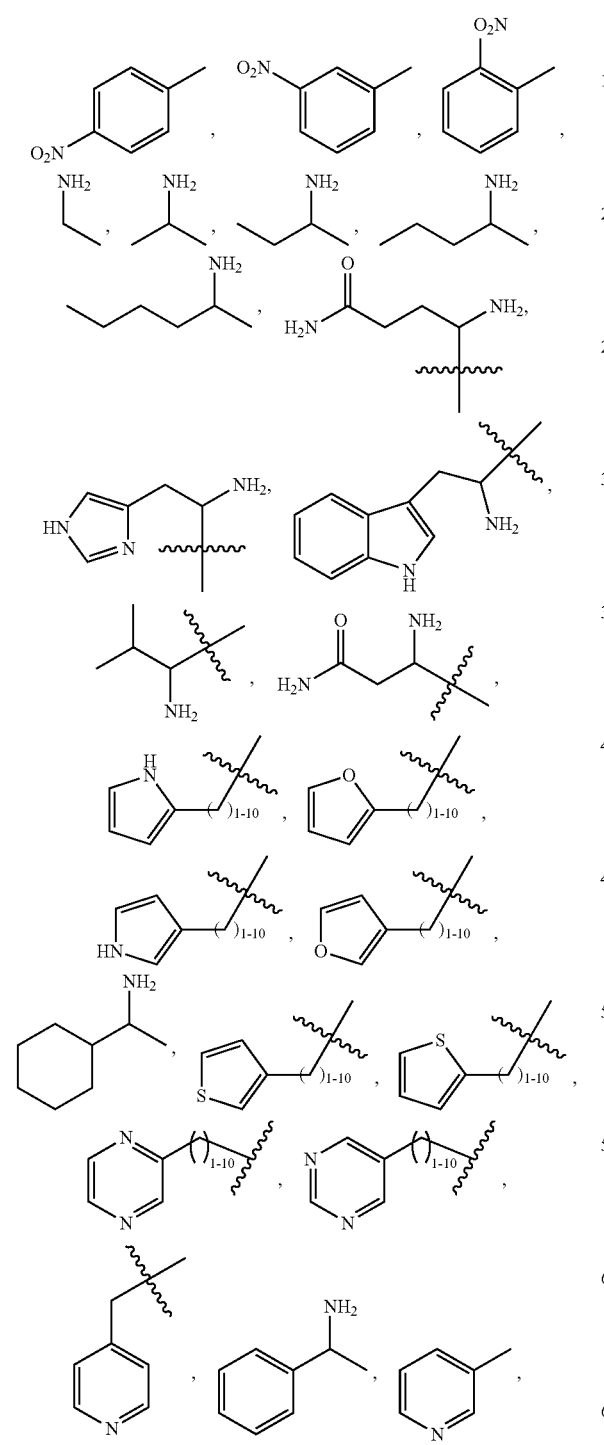

-continued

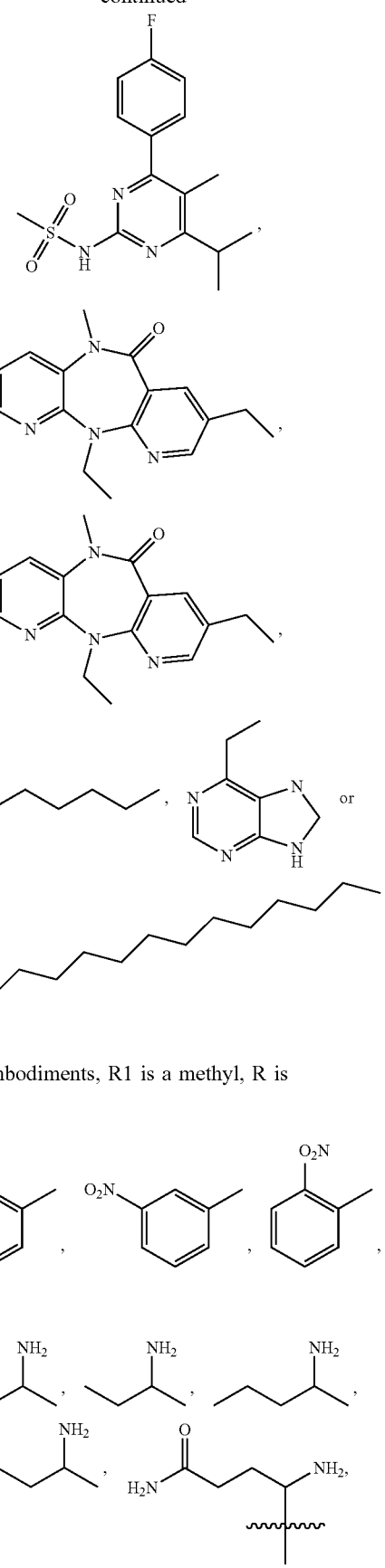

In other embodiments, R1 is a methyl, R is

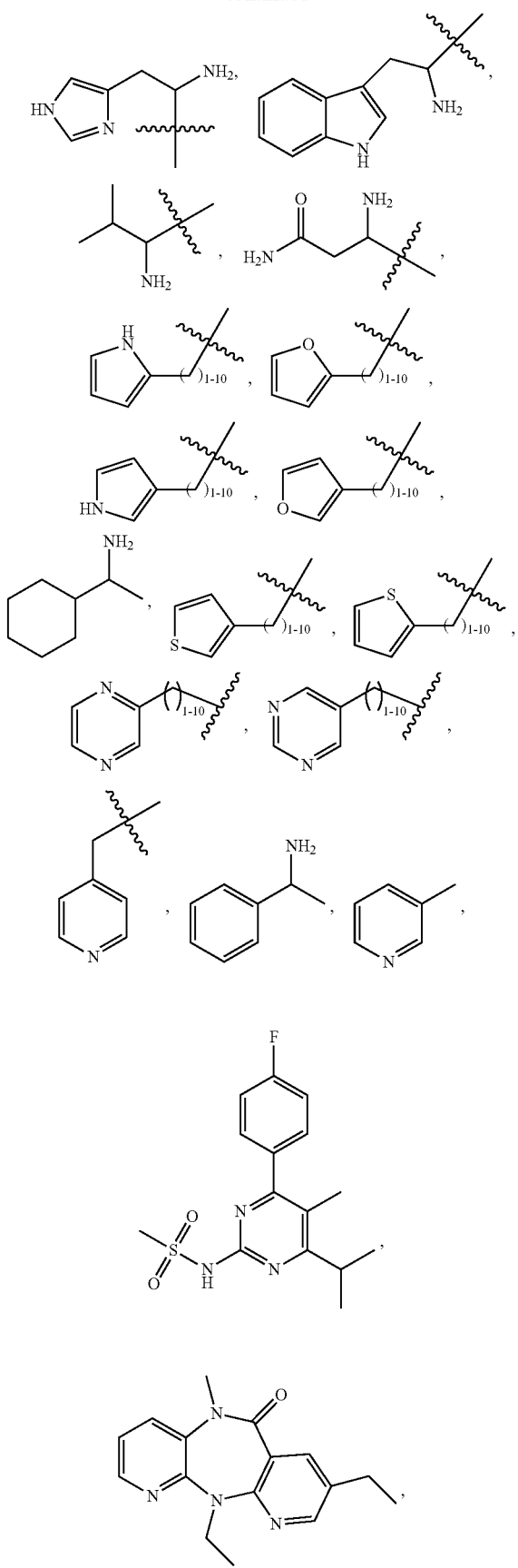
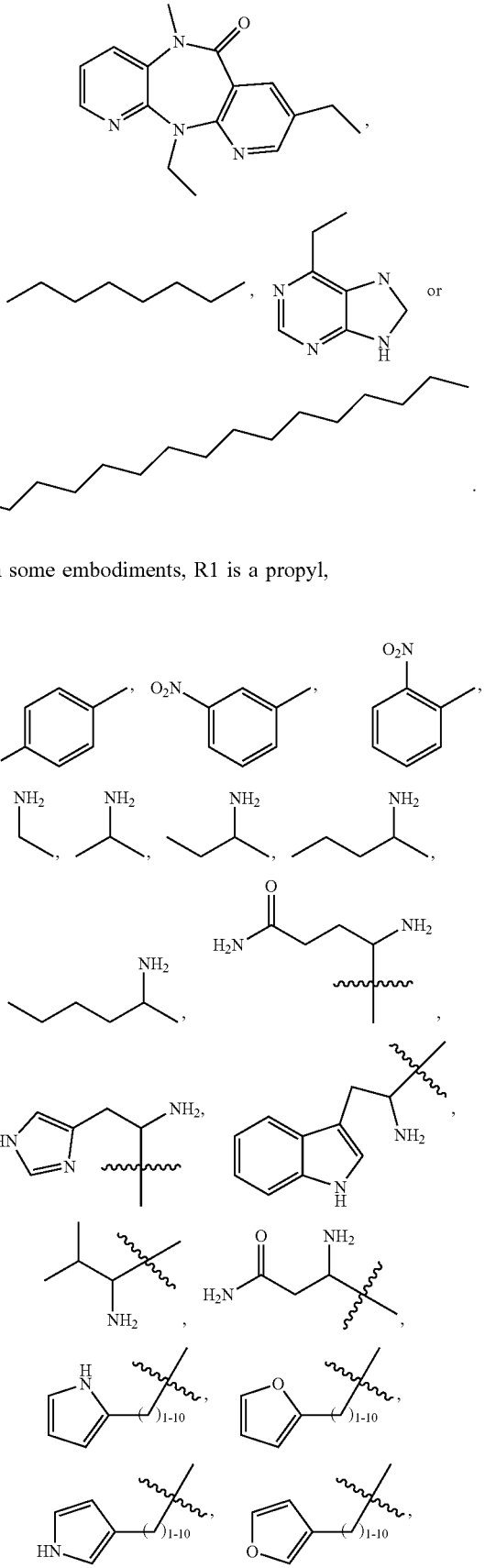
In some embodiments, R1 is a propyl,

-continued
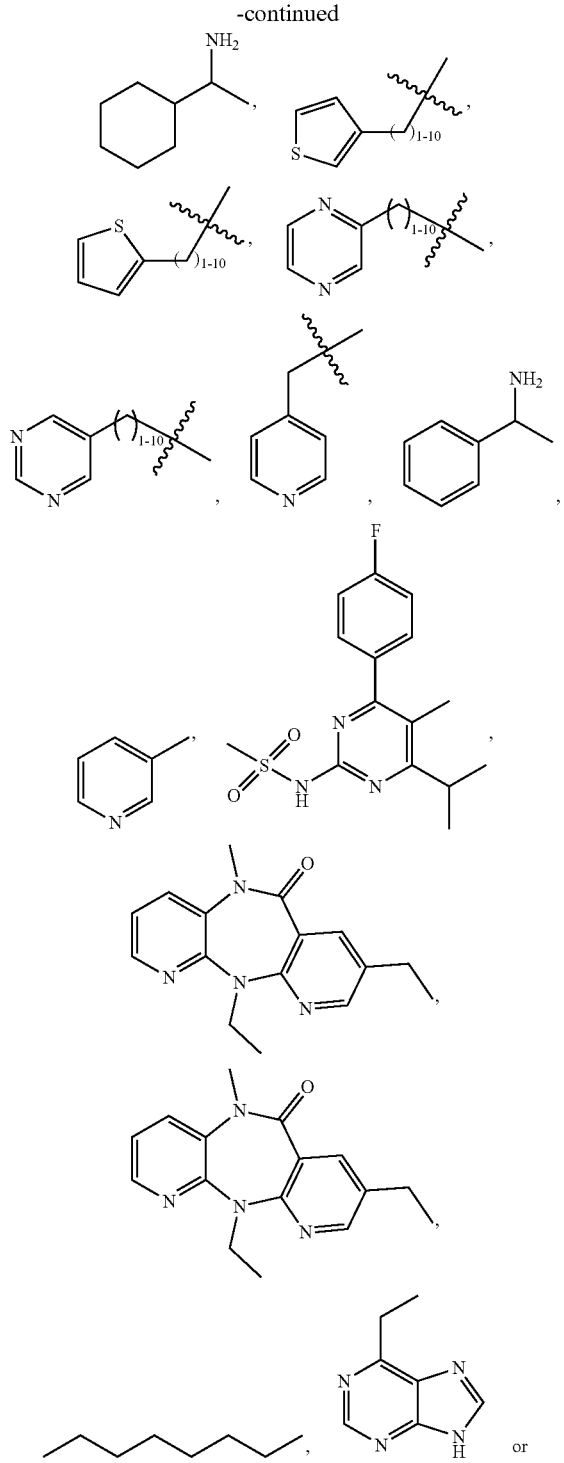
In some embodiments, R1 is a n-butyl,
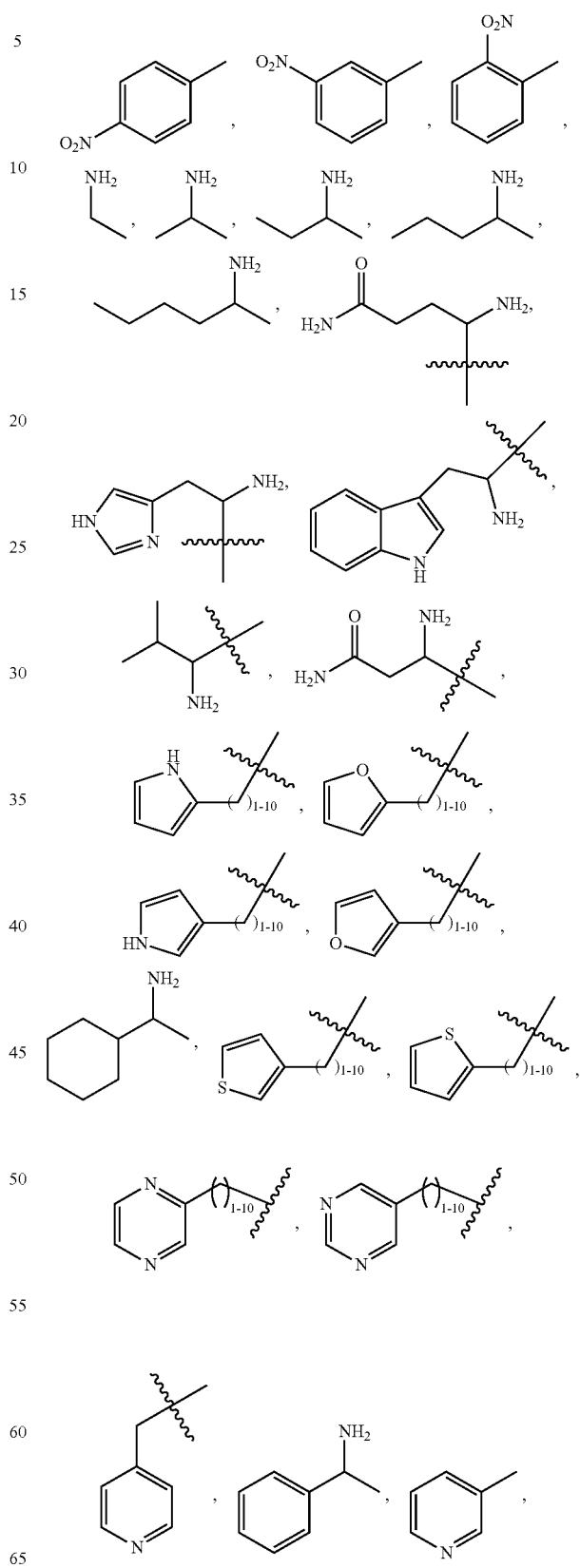

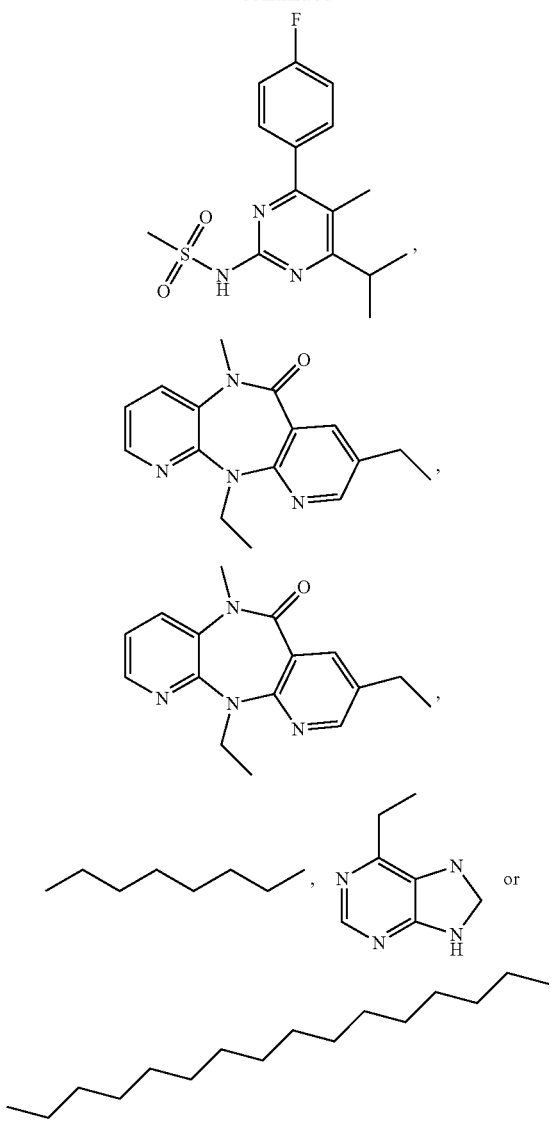
In some embodiments, R1 is a tert-butyl, R is
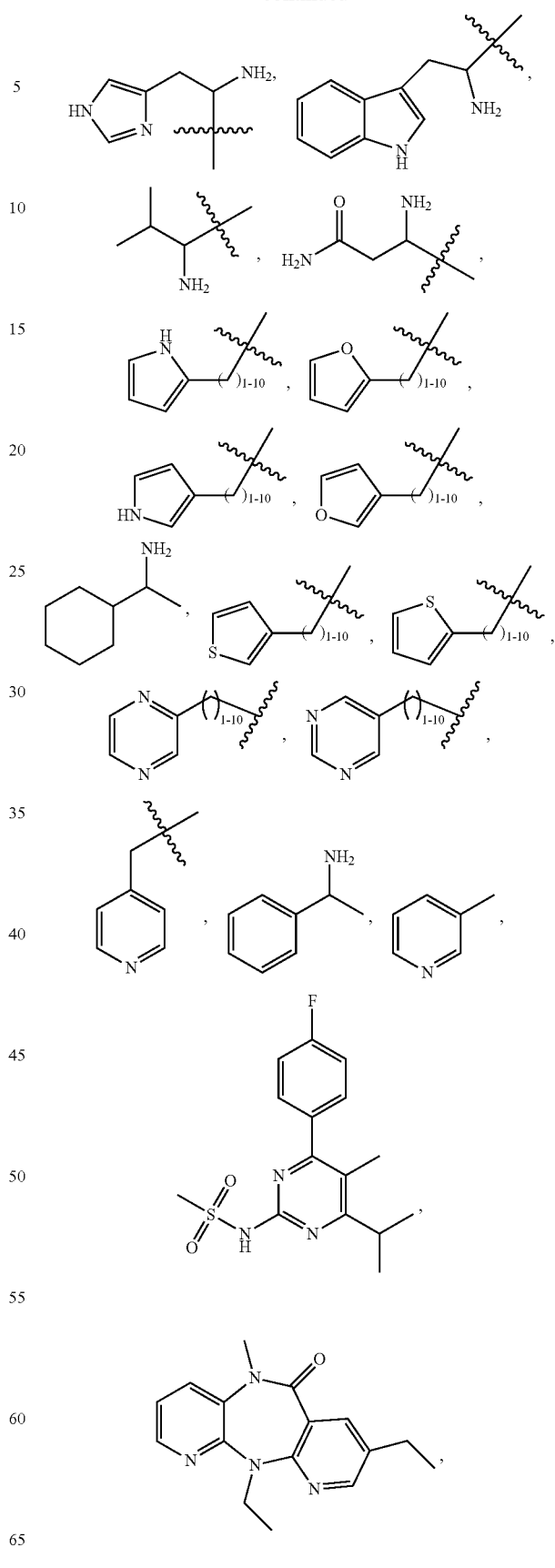

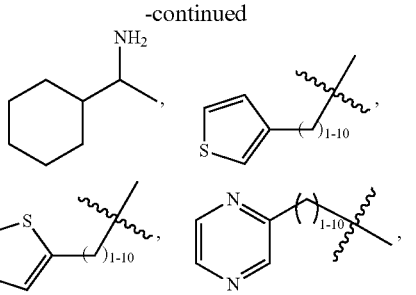
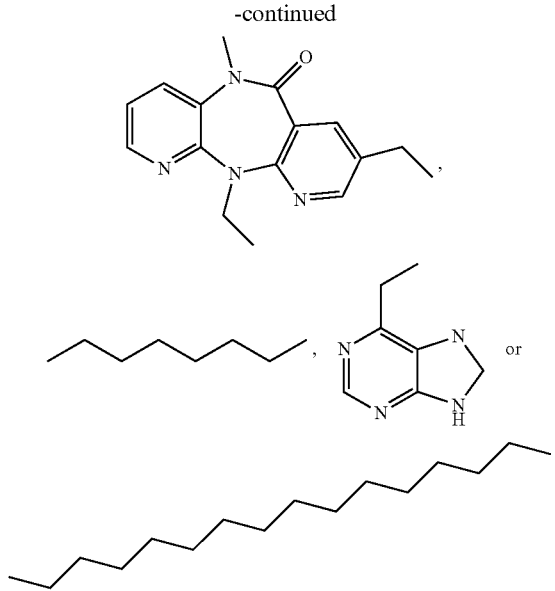
In some embodiments, R1 is a pentyl (especially a tert-amyl), R is
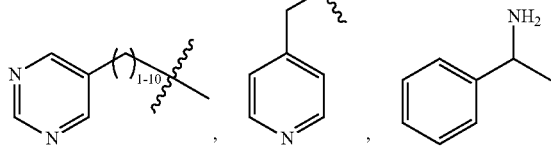
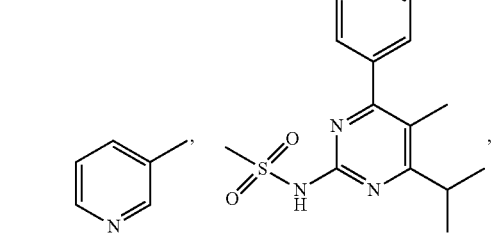
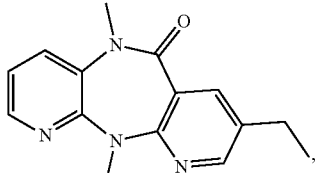
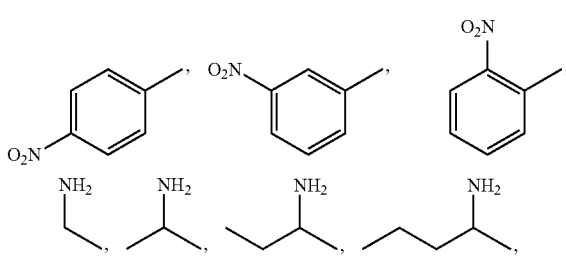
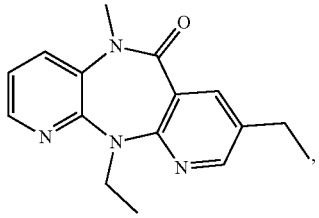
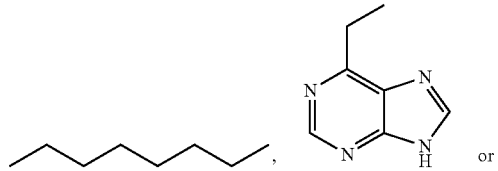
In some embodiments, R1 is hexyl $CH_3-(CH_2)_6-CH_2-$, R is

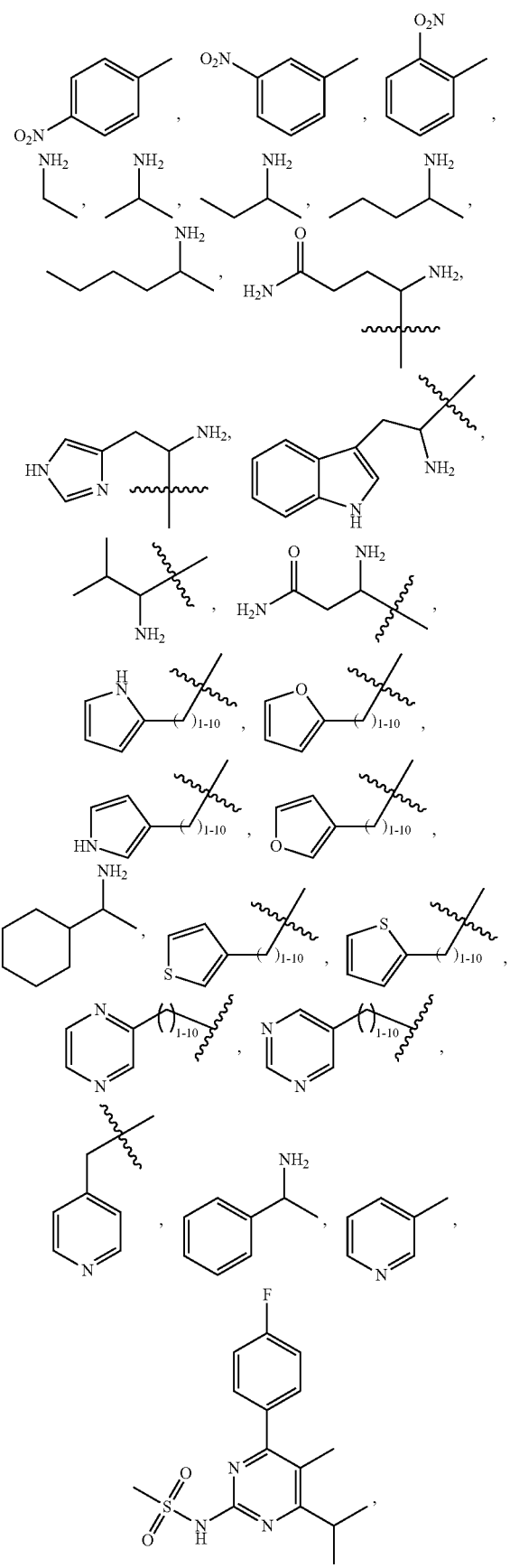
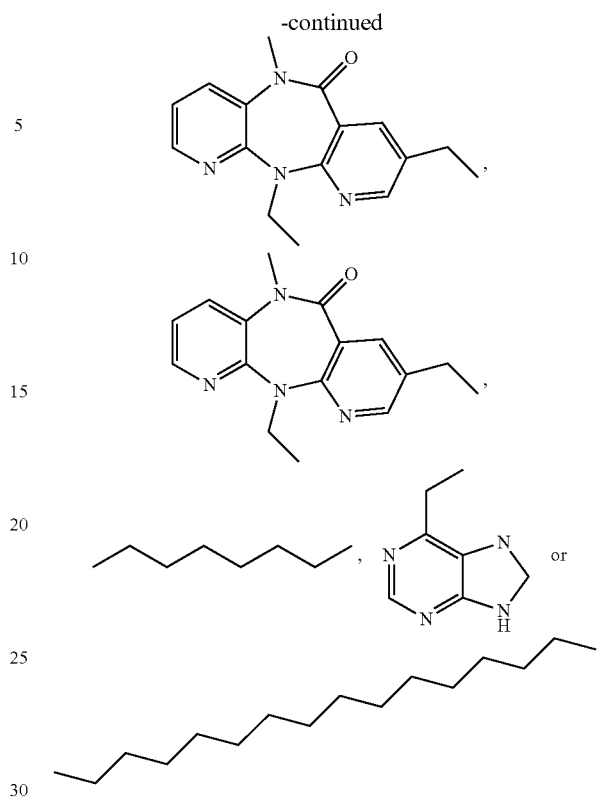

There is no correlation between the change of the R group and the change of the R1 group in the above different types of the esters, and the change of the R group and the change of the R1 group have no influence on the reduction process.

In order to further improve the reduction efficiency of the ester substrate by the reducing agent, in a preferred embodiment, in the borohydride reduction stabilizing system, the molar ratio of the borohydride reducing agent to the ester is 1.0~5.0:1, preferably 1.0~2.0:1, more preferably 1.5~2.0:1, preferably, the molar ratio of the stabilizing agent to the ester is 0.001~0.3:1, preferably 0.01~0.15:1, more preferably 0.01~0.05:1. Within the range of the amount ratio, the conversion rate and yield of the above ester reduced to the alcohol are relatively high.

In a preferred embodiment, the method is a continuous production method, and the continuous production may shorten a reaction period and improve the production efficiency.

In another preferred embodiment, the continuous production method includes: continuously adding the ester in parallel with the borohydride reduction stabilizing system to a reactor for reaction, herein the temperature of the reactor is 20~65° C., and preferably 40~60° C., and the retention time of the reaction is 15~120 min, and preferably 20~60 min.

The two raw materials are continuously added to the reactor for reaction, and the reactor temperature of the continuous reactor and the retention time of the reaction are controlled within the above preferred ranges, so that the reaction time required for the same production volume is short and the production period is apparently shortened, the relative batch reaction production efficiency is high (the total yield reaches 80-95%), and the process risk of operations is reduced. The continuous quenching operation is performed after the reaction, it avoids from generating more hydrogen in the batch, and has high process safety, thereby the yield is stable, and the repeatability is good. In addition, the continuous post-treatment operations are simple, the methanol may be recycled, and the cost is saved.

In the above continuous reaction process, the reaction system is performed in a protic solvent, and the specific type may be an existing one. In a preferred embodiment, before the step of continuously adding the ester to the reactor, the continuous production method further includes dissolving the ester into an alcohol solvent; and preferably, the alcohol solvent is a C1-C5 alcohol solvent, more preferably, the alcohol solvent is a C1-C3 alcohol solvent, and further preferably, the alcohol solvent is methanol solvent, ethanol solvent or isopropyl alcohol solvent.

It should be noted that the specific type of the alcohol solvent in the borohydride reduction stabilizing system and the specific type of the alcohol solvent for dissolving the ester substrate may be the same or different.

The beneficial effects of the present application are further described below in combination with the specific embodiments.

Embodiment 1

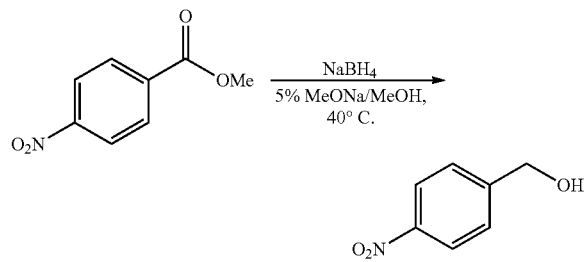

After methyl p-nitrobenzoate (110 g, 0.61 mol) is dissolved in methanol (440 mL, 4 V) and stirred, a pump A is used to pump it into a coil at a speed of 3.16 g/min. Sodium borohydride (33.86 g, 0.92 mol), and MeONa (0.98 g, 0.018 mol) are dissolved in methanol (110 mL, 1 V), and a pump B is used to pump it into a 240 mL φ3 coil at a speed of 0.84 g/min, the coil is immersed in a 40° C. oil bath, retention time is 60 min, an outlet is sampled by HPLC, and an outflowing system is put into a 1 L four-necked flask for quenching and extraction, and then it is distilled under a reduced pressure to obtain 79.3 g of a yellow liquid fraction product, the yield is 85%.

Embodiment 2

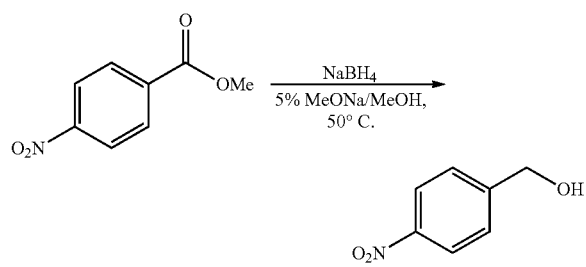

After methyl p-nitrobenzoate (110 g, 0.61 mol) is dissolved in methanol (440 mL, 4 V) and stirred, a pump A is used to pump it into a coil at a speed of 4.74 g/min. Sodium borohydride (33.86 g, 0.92 mol), and MeONa (0.98 g, 0.018 mol) are dissolved in methanol (110 mL, 1 V), and a pump B is used to pump it into a 240 mL φ3 coil at a speed of 1.26 g/min, the coil is immersed in a 50° C. oil bath, retention time is 40 min, an outlet is sampled by HPLC, and an outflowing system is put into a 1 L four-necked flask for quenching and extraction, and then it is distilled under a reduced pressure to obtain 84 g of a yellow liquid fraction product, the yield is 90.3%.

Embodiment 3

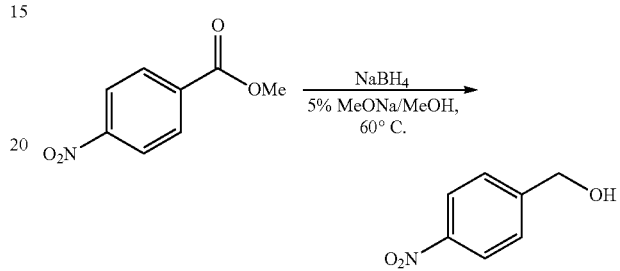

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (33.86 g, 0.92 mol), and MeONa (0.98 g, 0.018 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 88.6 g of a yellow liquid fraction product, the yield is 95%.

Embodiment 4

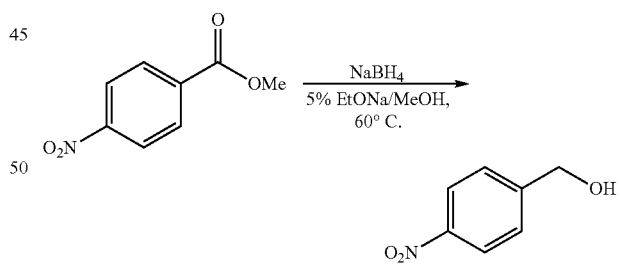

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (33.86 g, 0.92 mol), and EtONa (2.08 g, 0.018 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 85.8 g of a yellow liquid fraction product, the yield is 92%.

Embodiment 5

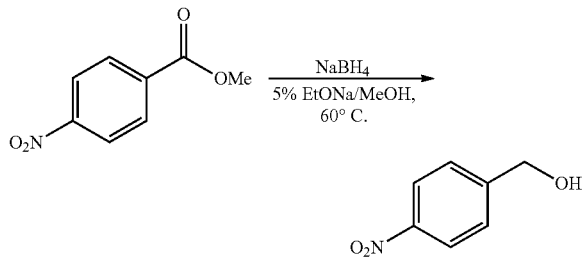

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (23.18 g, 0.61 mol), and MeONa (0.98 g, 0.018 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 70 g of a yellow liquid fraction product, the yield is 75%.

Embodiment 6

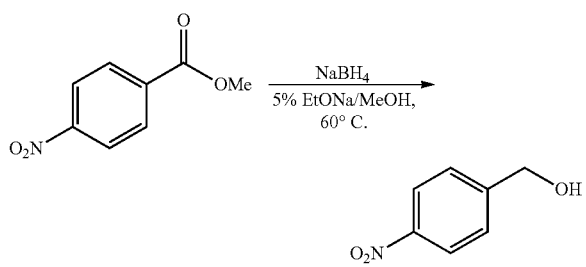

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (115.29 g, 3.05 mol), and MeONa (0.98 g, 0.018 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 60.6 g of a yellow liquid fraction product, the yield is 60.6%.

Embodiment 7

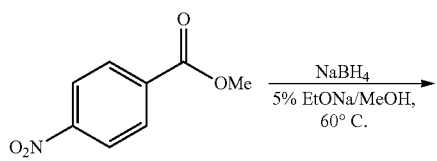

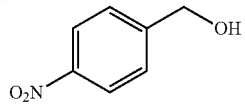

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (46.12 g, 1.22 mol), and MeONa (0.98 g, 0.018 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 78.3 g of a yellow liquid fraction product, the yield is 84%.

Embodiment 8

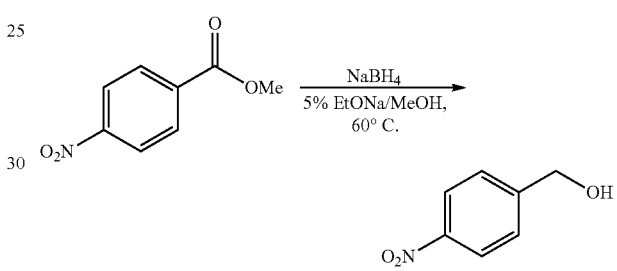

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (33.86 g, 0.92 mol), and MeONa (9.88 g, 0.183 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 57.8 g of a yellow liquid fraction product, the yield is 62%.

Embodiment 9

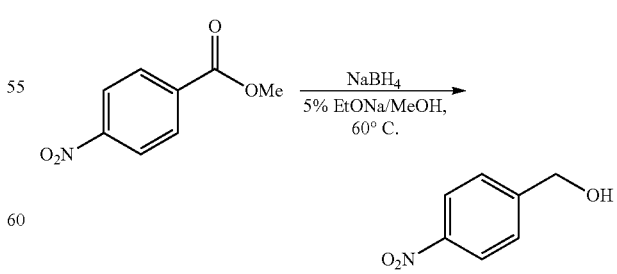

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (33.86 g, 0.92 mol), and MeONa (4.94 g, 0.092 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 65.3 g of a yellow liquid fraction product, the yield is 70%.

Embodiment 10

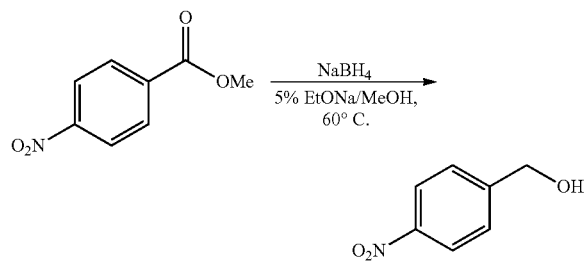

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (33.86 g, 0.92 mol), and MeONa (1.64 g, 0.03 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 74.6 g of a yellow liquid fraction product, the yield is 80%.

Embodiment 11

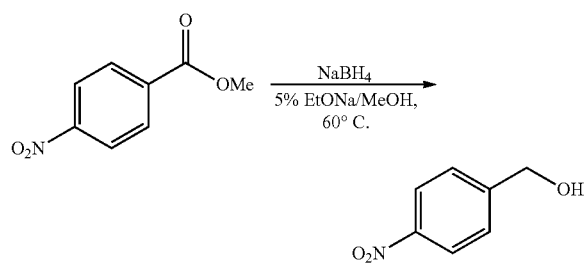

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (33.86 g, 0.92 mol), and MeONa (0.033 g, 0.0006 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 46.6 g of a yellow liquid fraction product, the yield is 50%.

Embodiment 12

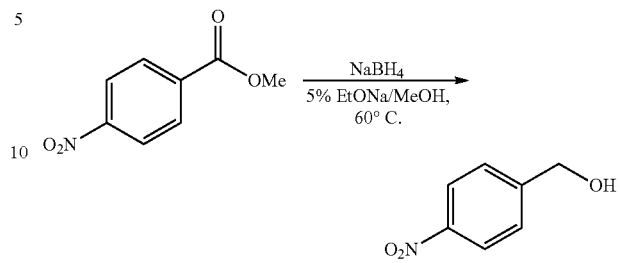

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (33.86 g, 0.92 mol), and MeONa (0.329 g, 0.0061 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 72.8 g of a yellow liquid fraction product, the yield is 78%.

Embodiment 13

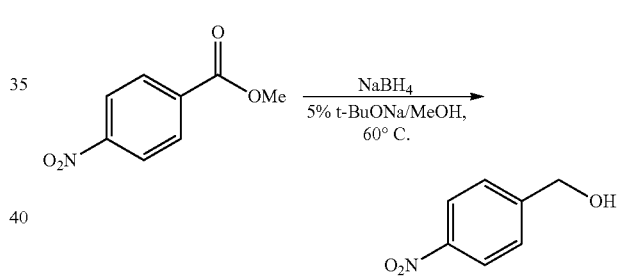

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (33.86 g, 0.92 mol), and t-BuONa (1.72 g, 0.018 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 80.2 g of a yellow liquid fraction product, the yield is 86%.

Embodiment 14

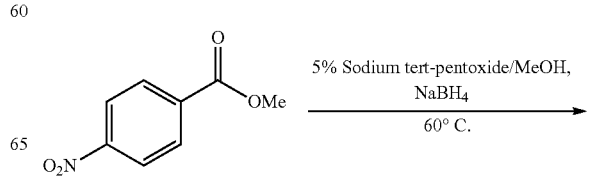

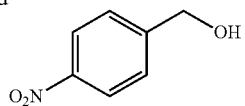

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (33.86 g, 0.92 mol), and sodium tert-pentoxide (1.98 g, 0.018 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is distilled under a reduced pressure to obtain 79.3 g of a yellow liquid fraction product, the yield is 85%.

Embodiment 15

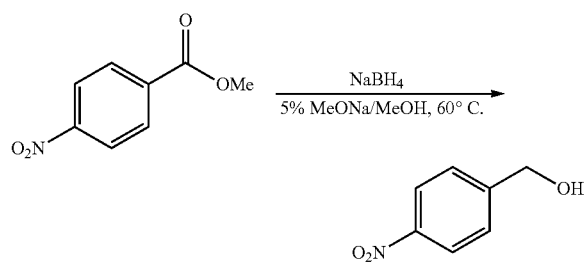

After methyl p-nitrobenzoate (110 g, 0.61 mol) is dissolved in methanol (440 mL, 4 V) and stirred, a pump A is used to pump it into a coil at a speed of 9.48 g/min. Sodium borohydride (33.86 g, 0.92 mol), and sodium ethoxide (2.08 g, 0.018 mol) are dissolved in methanol (110 mL, 1 V), and a pump B is used to pump it into a 240 mL φ3 coil at a speed of 2.52 g/min, the coil is immersed in a 60° C. oil bath, retention time is 20 min, an outlet is sampled by HPLC, and an outflowing system is put into a 1 L four-necked flask for quenching and extraction, and then it is performed by column chromatography to obtain 88.6 g of a product, the yield is 95%.

Embodiment 16

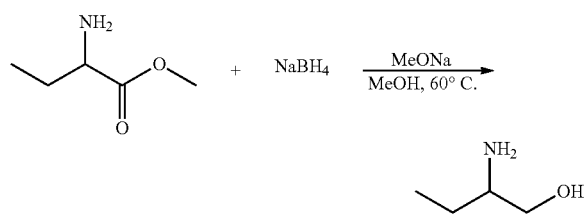

After methyl 2-aminobutyrate (100 g, 0.86 mol) is dissolved in methanol (400 mL, 4 V) and stirred, a pump A is used to pump it into a coil at a speed of 8.7 g/min. Sodium borohydride (47.36 g, 1.28 mol), and MeONa (1.38 g, 0.026 mol) are dissolved in methanol (100 mL, 1 V), and a pump B is used to pump it into a 240 mL φ3 coil at a speed of 2.3 g/min, the coil is immersed in a 60° C. oil bath, retention time is 20 min, an outlet is sampled by HPLC, and an outflowing system is put into a 1 L four-necked flask for quenching and extraction, and then it is performed by column chromatography to obtain 70 g of a product, the yield is 92%.

Embodiment 17

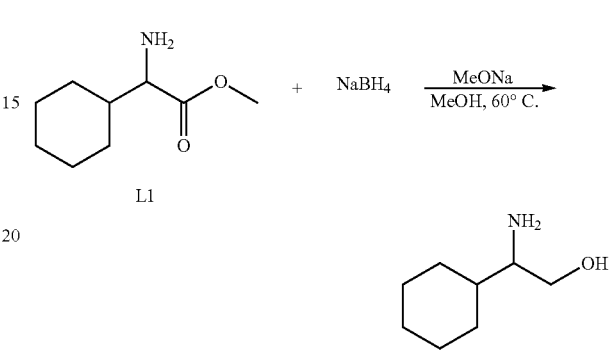

After L1 (100 g, 0.58 mol) is dissolved in methanol (400 mL, 4 V) and stirred, a pump A is used to pump it into a coil at a speed of 8.7 g/min. Sodium borohydride (32.45 g, 0.88 mol), and MeONa (0.95 g, 0.018 mol) are dissolved in methanol (100 mL, 1 V), and a pump B is used to pump it into a 240 mL φ3 coil at a speed of 2.3 g/min, the coil is immersed in a 60° C. oil bath, retention time is 20 min, an outlet is sampled by HPLC, and an outflowing system is put into a 1 L four-necked flask for quenching and extraction, and then it is performed by column chromatography to obtain 75.26 g of a product, the yield is 90%.

Embodiment 18

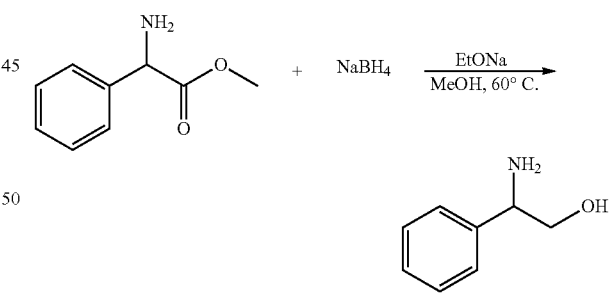

After phenylglycine methyl ester (100 g, 0.61 mol) is dissolved in methanol (400 mL, 4 V) and stirred, a pump A is used to pump it into a coil at a speed of 8.7 g/min. Sodium borohydride (33.86 g, 0.92 mol), and EtONa (1.24 g, 0.018 mol) are dissolved in methanol (100 mL, 1 V), and a pump B is used to pump it into a 240 mL φ3 coil at a speed of 2.3 g/min, the coil is immersed in a 60° C. oil bath, retention time is 20 min, an outlet is sampled by HPLC, and an outflowing system is put into a 1 L four-necked flask for quenching and extraction, and then it is performed by column chromatography to obtain 71.03 g of a product, the yield is 85%.

Embodiment 19

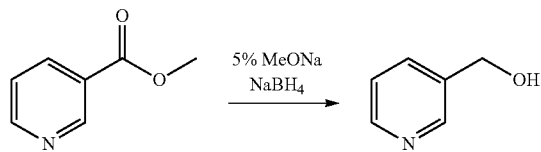

After methyl nicotinate (100 g, 0.73 mol) is dissolved in methanol (400 mL, 4 V) and stirred, a pump A is used to pump it into a coil at a speed of 8.7 g/min. Sodium borohydride (36.46 g, 0.87 mol), and MeONa (1.88 g, 0.036 mol) are dissolved in methanol (100 mL, 1 V), and a pump B is used to pump it into a 240 mL φ3 coil at a speed of 2.3 g/min, the coil is immersed in a 60° C. oil bath, retention time is 20 min, an outlet is sampled by HPLC, and an outflowing system is put into a 1 L four-necked flask for quenching and extraction, and then it is performed by column chromatography to obtain 74 g of a product, the yield is 93%.

Embodiment 20

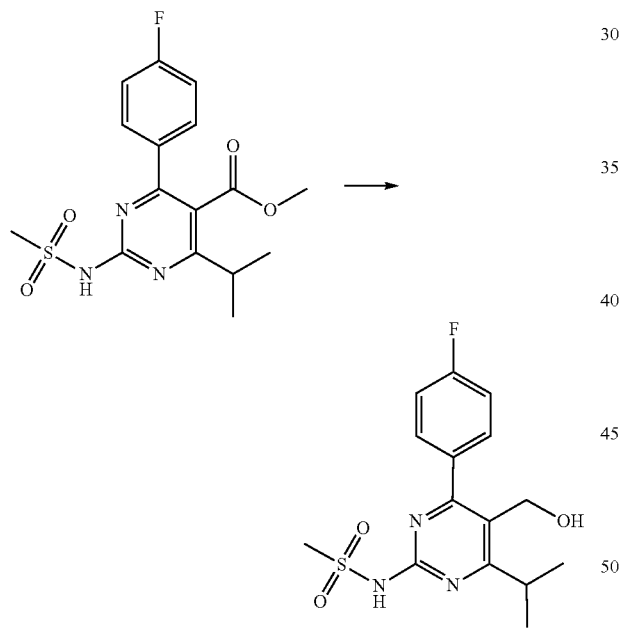

After methyl 4-(4-fluorophenyl)-6-isopropyl-2-(N-methyl-N-methanesulfonamido)-5-carboxylate-1-pyrimidine (224.1 g, 0.61 mol) is dissolved in methanol (900 mL, 4 V) and stirred, a pump A is used to pump it into a coil at a speed of 6.5 g/min. Sodium borohydride (33.86 g, 0.92 mol), and EtONa (1.24 g, 0.018 mol) are dissolved in methanol (224 mL, 1 V), and a pump B is used to pump it into a 240 mL φ3 coil at a speed of 1.5 g/min, the coil is immersed in a 40° C. oil bath, an outlet is sampled by HPLC, and an outflowing system is put into a 2 L four-necked flask for quenching and extraction, and then it is performed by column chromatography to obtain 175.8 g of a product, the yield is 85%.

Embodiment 21

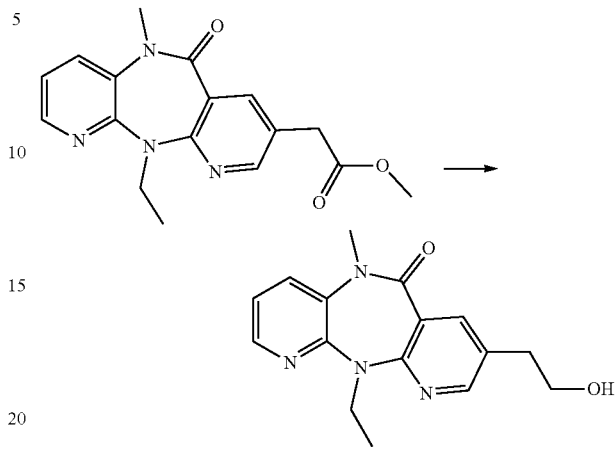

After 2-(11-ethyl-5-methyl-6-oxo-6,11-dihydro-5H-dipyrido[3,2-b:2',3'-e][1,4]diaza-8-yl) ethyl acetate (199 g, 0.61 mol) is dissolved in methanol (796 mL, 4 V) and stirred, a pump A is used to pump it into a coil at a speed of 6.4 g/min. Sodium borohydride (33.86 g, 0.92 mol), and EtONa (1.24 g, 0.018 mol) are dissolved in methanol (199 mL, 1 V), and a pump B is used to pump it into a 240 mL φ3 coil at a speed of 1.5 g/min, the coil is immersed in a 40° C. oil bath, an outlet is sampled by HPLC, and an outflowing system is put into a 2 L four-necked flask for quenching and extraction, and then it is performed by column chromatography to obtain 149.1 g of a product, the yield is 82%.

Embodiment 22

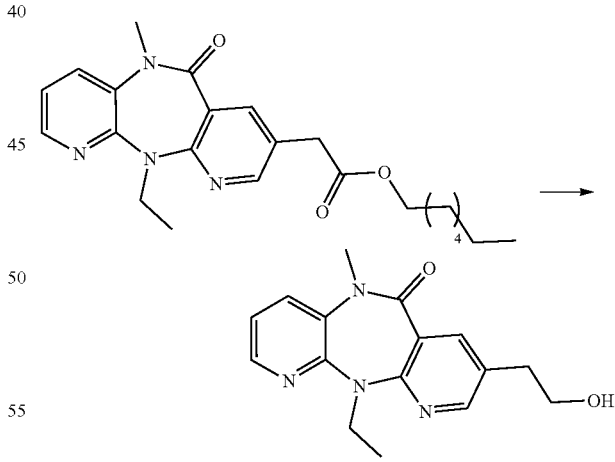

After 2-(11-ethyl-5-methyl-6-oxo-6,11-dihydro-5H-dipyrido[3,2-b:2',3'-e][1,4]diaza-8-yl)hexyl acetate (242 g, 0.61 mol) is dissolved in methanol (967 mL, 4 V) and stirred, a pump A is used to pump it into a coil at a speed of 5.8 g/min. Sodium borohydride (33.86 g, 0.92 mol), and EtONa (1.24 g, 0.018 mol) are dissolved in methanol (242 mL, 1 V), and a pump B is used to pump it into a 240 mL φ3 coil at a speed of 1.3 g/min, the coil is immersed in a 40° C. oil bath, an outlet is sampled by HPLC, and an outflowing system is put into a 2 L four-necked flask for quenching and extraction, and then it is performed by column chromatography to obtain 142 g of a product, the yield is 78%.

Embodiment 23

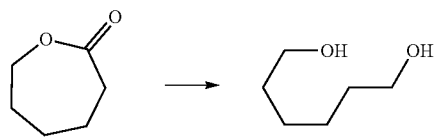 [SMILES: O=C1CCCCCO1 ; OCCCCCCO]

After 6-caprolactone (70 g, 0.61 mol) is dissolved in methanol (280 mL, 4 V) and stirred, a pump A is used to pump it into a coil at a speed of 5.9 g/min. Sodium borohydride (33.86 g, 0.92 mol), and EtONa (1.24 g, 0.018 mol) are dissolved in methanol (70 mL, 1 V), and a pump B is used to pump it into a 240 mL φ3 coil at a speed of 1.7 g/min, the coil is immersed in a 40° C. oil bath, an outlet is sampled by HPLC, and an outflowing system is put into a 2 L four-necked flask for quenching and extraction, and then it is performed by column chromatography to obtain 54 g of a product, the yield is 75%.

Embodiment 24

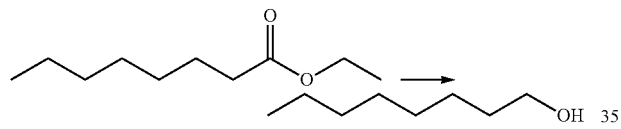

After ethyl caprylate (105 g, 0.61 mol) is dissolved in methanol (420 mL, 4 V) and stirred, a pump A is used to pump it into a coil at a speed of 5.6 g/min. Sodium borohydride (33.86 g, 0.92 mol), and EtONa (1.24 g, 0.018 mol) are dissolved in methanol (105 mL, 1 V), and a pump B is used to pump it into a 240 mL φ3 coil at a speed of 1.5 g/min, the coil is immersed in a 40° C. oil bath, an outlet is sampled by HPLC, and an outflowing system is put into a 2 L four-necked flask for quenching and extraction, and then it is performed by column chromatography to obtain 70 g of a product, the yield is 80%.

Embodiment 25

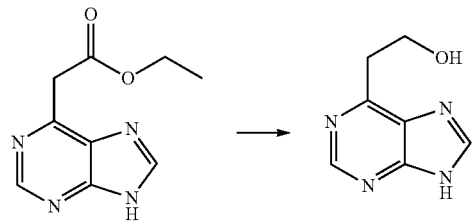

After purine ethyl acetate (126 g, 0.61 mol) is dissolved in methanol (504 mL, 4 V) and stirred, a pump A is used to pump it into a coil at a speed of 5.6 g/min. Sodium borohydride (33.86 g, 0.92 mol), and EtONa (1.24 g, 0.018 mol) are dissolved in methanol (126 mL, 1 V), and a pump B is used to pump it into a 240 mL φ3 coil at a speed of 1.5 g/min, the coil is immersed in a 40° C. oil bath, an outlet is sampled by HPLC, and an outflowing system is put into a 2 L four-necked flask for quenching and extraction, and then it is performed by column chromatography to obtain 86 g of a product, the yield is 86%.

Embodiment 26

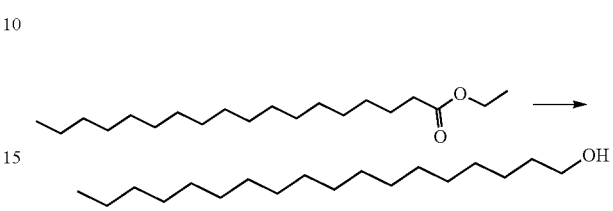

After ethyl octadecanoate (190.6 g, 0.61 mol) is dissolved in methanol (762 mL, 4 V) and stirred, a pump A is used to pump it into a coil at a speed of 6.1 g/min. Sodium borohydride (33.86 g, 0.92 mol), and EtONa (1.24 g, 0.018 mol) are dissolved in methanol (190.6 mL, 1 V), and a pump B is used to pump it into a 240 mL φ3 coil at a speed of 1.4 g/min, the coil is immersed in a 40° C. oil bath, an outlet is sampled by HPLC, and an outflowing system is put into a 2 L four-necked flask for quenching and extraction, and then it is performed by column chromatography to obtain 118.6 g of a product, the yield is 72%.

Embodiment 27

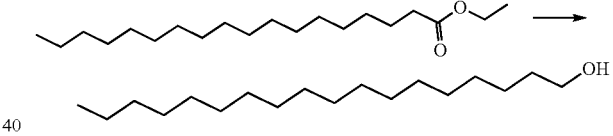

After ethyl octadecanoate (190.6 g, 0.61 mol) is dissolved in methanol (762 mL, 4 V) and stirred, a pump A is used to pump it into a coil at a speed of 6.1 g/min. Potassium borohydride (49.62 g, 0.92 mol), and EtONa (1.24 g, 0.018 mol) are dissolved in methanol (190.6 mL, 1 V), and a pump B is used to pump it into a 240 mL φ3 coil at a speed of 1.6 g/min, the coil is immersed in a 40° C. oil bath, an outlet is sampled by HPLC, and an outflowing system is put into a 2 L four-necked flask for quenching and extraction, and then it is performed by column chromatography to obtain 115.3 g of a product, the yield is 70%.

Embodiment 28

After methyl p-nitrobenzoate (110 g, 0.61 mol) is dissolved in methanol (550 mL, 4 V) and stirred, sodium methoxide (1.65 g, 0.031 mol) is added, and stirred uniformly, it is heated. At 40° C., sodium borohydride (34.6 g, 0.91 mol) is added in batches, the temperature is kept and it is stirred for 0.5 h, the system may release hydrogen, after the TCL raw material disappears, water is added to quench, after most of the methanol is concentrated, it is extracted with MTBE, and then it is distilled under a reduced pressure to obtain 76.36 g of a yellow liquid fraction product, and the yield is 83%.

Contrast Example 1

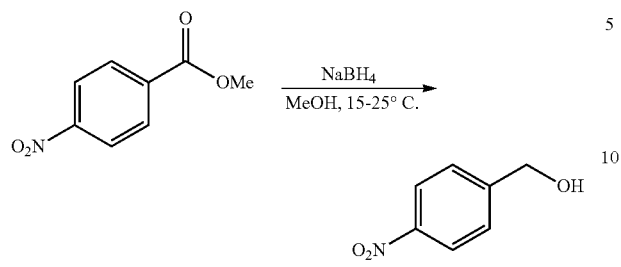

After methyl p-nitrobenzoate (110 g, 0.61 mol) is dissolved in methanol (550 mL, 4 V) and stirred, sodium borohydride (69.17 g, 1.83 mol) is added in batches at 40° C., the temperature is kept and it is stirred for 3 h, the system may release hydrogen, after the TCL raw material disappears, water is added to quench, after most of the methanol is concentrated, it is extracted with MTBE, and then it is distilled under a reduced pressure to obtain 69 g of a yellow liquid fraction product, and the yield is 75%.

It may be seen from the above descriptions that the above embodiments of the present invention achieve the following technical effects: by adding the alkali metal salt of the alcohol (such as sodium alkoxide or potassium alkoxide) on the basis of an existing sodium/potassium borohydride reducing agent, the corresponding reducing agent may be kept stable without being easily decomposed. On the one hand, the reducing activity may be maintained and the excessive use condition may be reduced, and on the other hand, the production of the hydrogen may be reduced, and the process risk may be reduced.

In addition, the alkali metal borohydride reducing agent stabilized by the alkali metal salt of the alcohol of the present application is used in the production process for continuously reducing the ester to the alcohol. Compared with the batch reaction, the continuous reaction shortens the overall reaction time, the production period is accelerated and the production efficiency is improved. Moreover, the reducing agent may be continuously quenched after the continuous reaction is completed, the post-treatment is simple, and the risk that it is easy to explode while quenched for one time because the more hydrogen is generated in the batch reaction is avoided, and the process safety is high. In addition, the alcohol solvent may also be recycled, the cost is saved.

The above are only preferred embodiments of the present invention, and are not used to limit the present invention. For those skilled in the art, the present invention may have various modifications and changes. Any modifications, equivalent replacements, improvements and the like made within the spirit and principle of the present invention should be included in a scope of protection of the present invention.

What is claimed is:

1. A method for reducing an ester to an alcohol, wherein the method comprises reducing an ester to an alcohol with a borohydride reduction stabilizing system, wherein the borohydride reduction stabilizing system comprises:

a borohydride reducing agent, wherein the borohydride reducing agent is sodium borohydride or potassium borohydride; and a stabilizing agent for stabilizing the borohydride reducing agent, wherein the stabilizing agent is an alkali metal salt of an alcohol;

wherein the molar ratio of the borohydride reducing agent to the stabilizing agent is 1.5-2.0:0.01-0.05;

wherein the ester has a structure represented by formula (I):

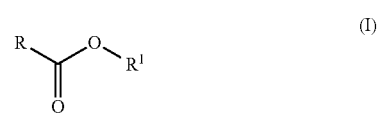

wherein R1 is C1-C12 alkyl, R is

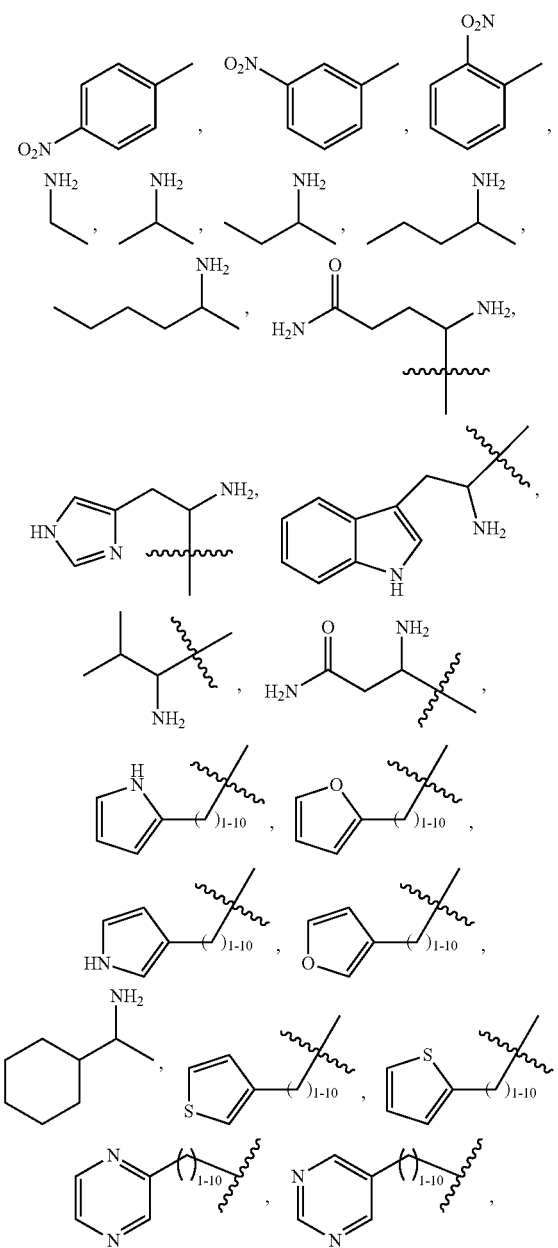

-continued

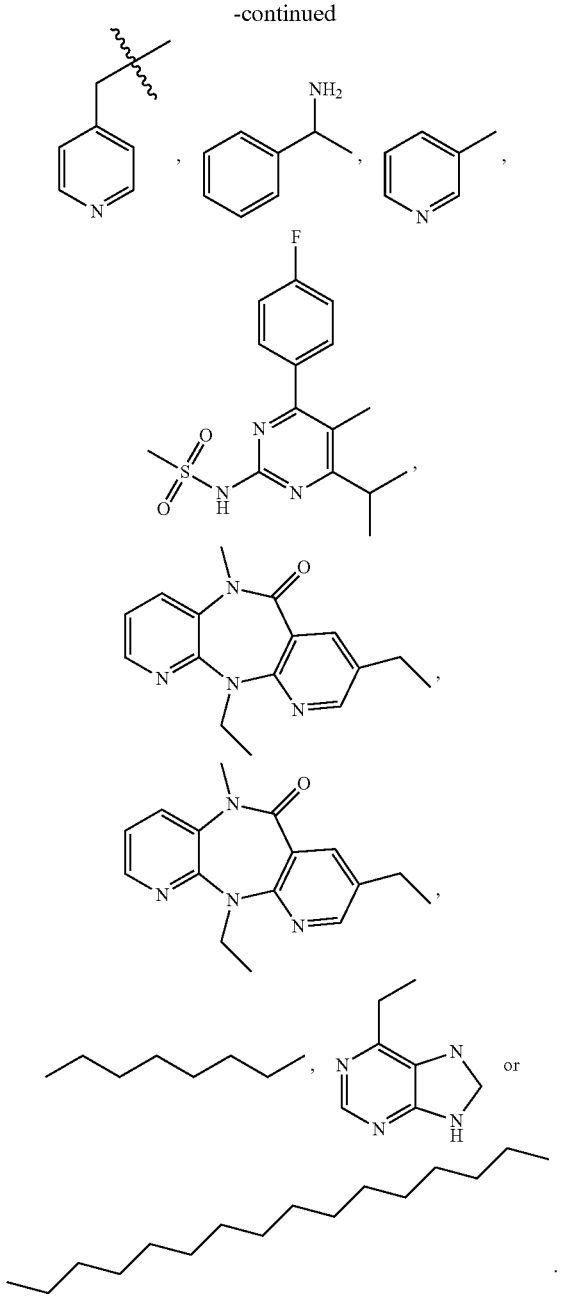

wherein the method is a continuous production method, and the continuous production method comprises:

continuously adding the ester in parallel with the borohydride reduction stabilizing system to a reactor for reaction, wherein the temperature of the reactor is 40~60° C., and the retention time of the reaction is 20~60 min.

2. The method according to claim 1, wherein in the borohydride reduction stabilizing system, a molar ratio of the borohydride reducing agent to the ester is 1.0-5.0:1, and a molar ratio of the stabilizing agent to the ester is 0.001-0.3:1.

3. The method according to claim 1, wherein before continuously adding the ester to the reactor, the continuous production method further comprises dissolving the ester into an alcohol solvent; and wherein, the alcohol solvent is a C1-C5 alcohol solvent.

4. The method according to claim 1, wherein the stabilizing agent is a sodium salt or potassium salt of any one or more alcohols selected from the group consisting of methanol, ethanol, butanol and pentanol; and wherein, the butanol is tert-butanol, and the pentanol is tert-pentanol.

5. The method according to claim 1, wherein the group has 1~20 carbon atoms.

6. The method according to claim 2, wherein the molar ratio of the borohydride reducing agent to the ester is 1.0-2.0:1.

7. The method according to claim 6, wherein the molar ratio of the borohydride reducing agent to the ester is 1.5-2.0:1.

8. The method according to claim 2, wherein the molar ratio of the stabilizing agent to the ester is 0.01-0.15:1.

9. The method according to claim 1, wherein the stabilizing agent is a sodium salt or potassium salt of an alcohol.

10. The method according to claim 3, wherein the alcohol solvent is a C1-C3 alcohol solvent.

11. The method according to claim 3, wherein the alcohol solvent is methanol solvent, ethanol solvent or isopropyl alcohol solvent.

12. The method according to claim 8, wherein the molar ratio of the stabilizing agent to the ester is 0.01-0.05:1.

* * * * *